United States Patent [19]
Adams
[11] Patent Number: 4,755,628
[45] Date of Patent: * Jul. 5, 1988

[54] PROCESS FOR DEHALOGENATING HYDROCARBONS

[75] Inventor: Edward C. Adams, Barto, Pa.
[73] Assignee: AMOP, Inc., Pennington, N.J.

[*] Notice: The portion of the term of this patent subsequent to Aug. 14, 2001 has been disclaimed.

[21] Appl. No.: 623,489

[22] Filed: Jun. 22, 1984

Related U.S. Application Data

[63] Continuation-in-part of Ser. No. 524,133, Aug. 17, 1983, Pat. No. 4,465,590.

[51] Int. Cl.[4] ........................ C07C 1/20; C10G 17/00
[52] U.S. Cl. ........................ 585/469; 208/262
[58] Field of Search ........................ 208/262; 585/469

[56] References Cited

U.S. PATENT DOCUMENTS

| | | | |
|---|---|---|---|
| 4,337,368 | 6/1982 | Pytlewski et al. | 568/730 |
| 4,340,471 | 7/1982 | Jordan | 210/101 |
| 4,377,471 | 3/1983 | Brown | 208/262 |
| 4,379,752 | 4/1983 | Norman | 210/712 |
| 4,514,294 | 4/1985 | Layman et al. | 210/87 |
| 4,592,844 | 6/1986 | Layman et al. | 210/709 |

*Primary Examiner*—Curtis R. Davis
*Attorney, Agent, or Firm*—Spencer & Frank

[57] ABSTRACT

A process for dehalogenating halogenated hydrocarbons is disclosed wherein after vacuum dewatering of the hydrocarbon it is admixed in a reaction vessel with a dispersion of sodium of particle sizes of 10 microns or less, heated above 97.7° C. to liquify the sodium and the atmosphere above the admixture is converted to argon gas. Thereafter the admixture may be saturated with hydrogen by dissolution to facilitate the reaction. The reaction products are cooled, and the dehalogenated hydrocarbon is removed after filtration.

11 Claims, No Drawings

PROCESS FOR DEHALOGENATING HYDROCARBONS

CROSS-REFERENCES

This application is a continuation-in-part of Ser. No. 524,133, filed Aug. 17, 1983, now U.S. Pat. No. 4,465,590.

FEDERALLY-SPONSORED RIGHTS

The invention herein was made without any Federal sponsorship or contribution.

BACKGROUND OF THE INVENTION

1. The Field of the Invention.

The field of the invention relates to the dehologenating of halogenated hydrocarbons by their treatment with liquid sodium. Accordingly the general objectives of the present invention are to provide a novel and improved method of such character.

2. Description of the Prior Art.

The background art of the invention reveals the well-known Wurtz-Fitting reaction, and its precursor the Wurtz reaction, in which soduim is reacted with an alkyl or aryl halide and more recently, commercially, various attempts at elimination and destruction of polychlorinated bi-phenyls (PCB's), highly toxic environmental polutants, from oil, and particularly transformer oil. Reference is made to U.S. Pat. Nos. 4,337,368 to Pytlewski et al, 4,340,471 to Jordan, 4,377,471 to Brown and 4,379,752 to Norman. These methods are generally characterized by reactions which attempt to strip away chlorine from the aromatic ring structure of PCB's leaving, inter alia, a non-chlorinated byphenyl, benzene, chloro-benzene, some of which may be themselves environmentally harmful, and sodium chloride.

The Wurtz-Fitting reaction is well-known and may be summarized generally by:

1.

$$RX+Na \rightarrow RNaX+H^{+}$$

2.

$$RNaX+H^{+} \rightarrow RH+NaX$$

or alternatively:

2a.

$$2RNaX \rightarrow R-R+2NaX.$$

The reaction is conducted at temperatures above 97.7° C., the melting point of sodium. A stoichiometric amount of sodium is added to the organic halide based upon an estimate of the amount of halogen to be removed. An excess of sodium is desirable and may be readily removed by subsequent cooling, filtration and destruction by, for examplo, sulfuric acid.

In the laboratory, the Wurtz-Fitting reaction is characterized by poor yields and other disappointing results.

One of the basic problems encountered, which the present invention solves, has been the uncontrolled formation of undesirable free radicals occasioned by the inadvertent presence of various contaminants, as well as sodium, and a consequent undesirble polymerization or combination of such radicals.

An objective of the present invention is to increase the yield of de-halogenated hydrocarbons. A further object is to reduce large polymer by-products possible in the reaction simultaneously therewith by controlled hydrogenation of free radicals which are the natural remnants of the destructive reaction process. Previous efficiencies of reaction have been reported up to 75%, based upon starting temperature, time, and purity of the hydrocarbonaceous component.

Yields in excess of 99% have been observed by the present invention. Factors previously taken into account by those skilled in the art have been particle size of the sodium prior to its liquifaction, control of the contact of pure sodium with air prior to its addition into the reaction vessel, the effect of moisture upon sodium generally and the recommended use of nitrogen as a blanket over the surface of the reactants. Particular importance has been attached to the maintenance of pre-liquidus sodium at particle sizes below 10 microns in diameter. Attention is directed to U.S. Pat. No. 4,379,752 to Norman in which reference is made to the text of Fatt and Tashima, "Alkali Metal Dispersions," Van Nostrand (New York, 1961). The hazard of sodium in the presence of moisture wherein the dangerous evolution of hydrogen gas and the formation of sodium hydroxide is well-known. However, those ordinarily skilled in the art invariably fail to de-water the halide as a preliminary step but sometimes do so post-reaction. Such a failure, however, causes the unwanted consumption of sodium. The presence of the hydroxide also appears to inhibit the dehalogenation.

The use of nitrogen, in lieu of air, over the surface of the reaction medium, has been thought to eliminate problems caused by moisture in the air as well as oxygen in contact with the sodium wherein sodium oxide is rapidly and undesirably formed. Your inventor has found that nitrogen will in fact substantially affect the reactive process and it must be avoided if yields above 75% are to be had. Use of dry argon or helium in place of the nitrogen as the current invention teaches has a significant effect on yield allowing achievement in excess of 99%.

The method disclosed in this application provides an efficient and rapid means for the destructive dehalogenation of hydrocarbons.

SUMMARY OF THE INVENTION

The invention may be summarized as a process in which a halogenated hydrocarbon is first treated under moderate vacuum and elevated temperature to separate by vacuum distillation water, solvents and, if present, light fraction hydrocarbonaceous impurities. It is then admixed and reacted with liquid sodium whose pre-liquidus state is of a particle size of less than 10 microns in diameter. Thereafter, in a blanket of argon gas, the reactant mixture is raised further in temperature and subjected to agitation. To accelerate the reaction, hydrogen gas optionally is dissolved thereafter by entrainment to suppress the formation of undesirable contaminants and polymers. In a very short period of time, chemical analysis reveals, surprisingly, the almost total elimination of halogenated hydrocarbons. Thereupon the reactants are cooled and filtered. The waste products are mostly sodium chloride and a small amount of polymerized dehalogenated hydrocarbon depending on the composition of the original.

DESCRIPTION OF DRAWINGS

There are no drawings presented herewith.

DESCRIPTION OF THE PREFERRED EMBODIMENT

The preferred embodiment of the present invention is described.

A measured amount of organic halide, with an estimate made thereon of the halogen therein contained, is put in a vessel, heated to 75° C. and subjected to a standing vacuum in excess of 27 inches. In this environment de-watering takes place. When this is complete, the vacuum is released and a sodium despersion of a particle size of 10 microns or less is added. The sodium is stoichiometrically calculated on the basis of 23 g to the gram atomic equivalent of each halogen present. The atmosphere above the reactants is simultaneously flooded with argon, the vessel sealed and the temperature of the vessel raised to 105°-120° commence the reaction.

Upon completion, generally 30-45 minutes, the vessel is cooled, the sodium halide, excess sodium and any polymers are filtered off and the remaining liquid, consisting of dehalogenated hydrocarbon, is preserved.

What claimed is:

1. An improved method for the dehalogenation of halogenated hydrocarbonaceous substances which comprises:

(a) depositing in a reaction vessel a measured weight of halogenated hydrocarbon containing a known amount of halogen;
(b) causing a vacuum to exist in the reacting vessel by evaluating air therefrom;
(c) raising the temperature in the vessel;
(d) de-watering the hydrocarbon;
(e) releasing the vacuum to near ambient atmospheric pressure while simultaneously adding an inert gas thereto to form an atmosphere above the hydrocarbon such that air is excluded;
(f) adding to the reacting vessel an amount of sodium sufficient to destroy the halogen therein contained and creating a mixture of sodium and hydrocaron;
(g) raising the temperature of the mixture to a point which maintains the sodium in liquid condition;
(h) reacting the hydrocarbon with the sodium until the halide is removed;
(i) cooling the mixture;
(j) separating the reacted hydrocarbon from other reactants.

2. As in claim 1, wherein, after step (b) thereof, the step of dissolving hydrogen in the mixture is added.

3. As in claim 2, dissolving an amount of hydrogen gas in the mixture sufficient to saturate it with hydrogen.

4. As in claim 1 at (f) thereof adding an amount of sodium at a ratio of 23 g sodium per gram atom of halogen.

5. As in claim 4, wherein the sodium is of a particle size below 10 microns in diameter.

6. As in claim 1 at (b) thereof, causing a vacuum to exist at 25 to 29 inches of mercury.

7. As in claim 1 at (c) thereof, raising the temperature to 75°-80° C.

8. As in claim 1 at (g) thereof, raising the temperature to 105°-130° C.

9. As in claim 1, at (e) thereof, wherein the inert gas is chosen from a group consisting of helium, argon, krypton or neon.

10. As in claim 9, wherein the gas is argon.

11. As in claim 1, wherein by adding after step (g) thereof the step of agitation is added.

* * * * *